US00PP37795P2

(12) United States Plant Patent
Nigon

(10) Patent No.: US PP37,795 P2
(45) Date of Patent: Oct. 20, 2026

(54) ***ANEMONE* PLANT NAMED 'IFANDWNB'**

(50) Latin Name: *Anemone hupehensis*
Varietal Denomination: IFANDWNB

(71) Applicant: INNOFLORA PLANT BREEDING B.V., Heerhugowaard (NL)

(72) Inventor: Maxime Jean Nigon, Heerhugowaard (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 19/554,167

(22) Filed: Mar. 2, 2026

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP34,891 P2 * 1/2023 Spil ..... A01H 6/72
Plt./263.1

* cited by examiner

*Primary Examiner* — Karen M Redden
(74) *Attorney, Agent, or Firm* — C. Anne Whealy

(57) ABSTRACT

A new and distinct cultivar of *Anemone* plant named 'IFANDWNB', characterized by its compact, upright and uniform plant habit; moderately vigorous to vigorous growth habit; early and freely flowering habit; long flowering period; single-type flowers that are purplish red in color; and good garden performance.

3 Drawing Sheets

Figure 1:
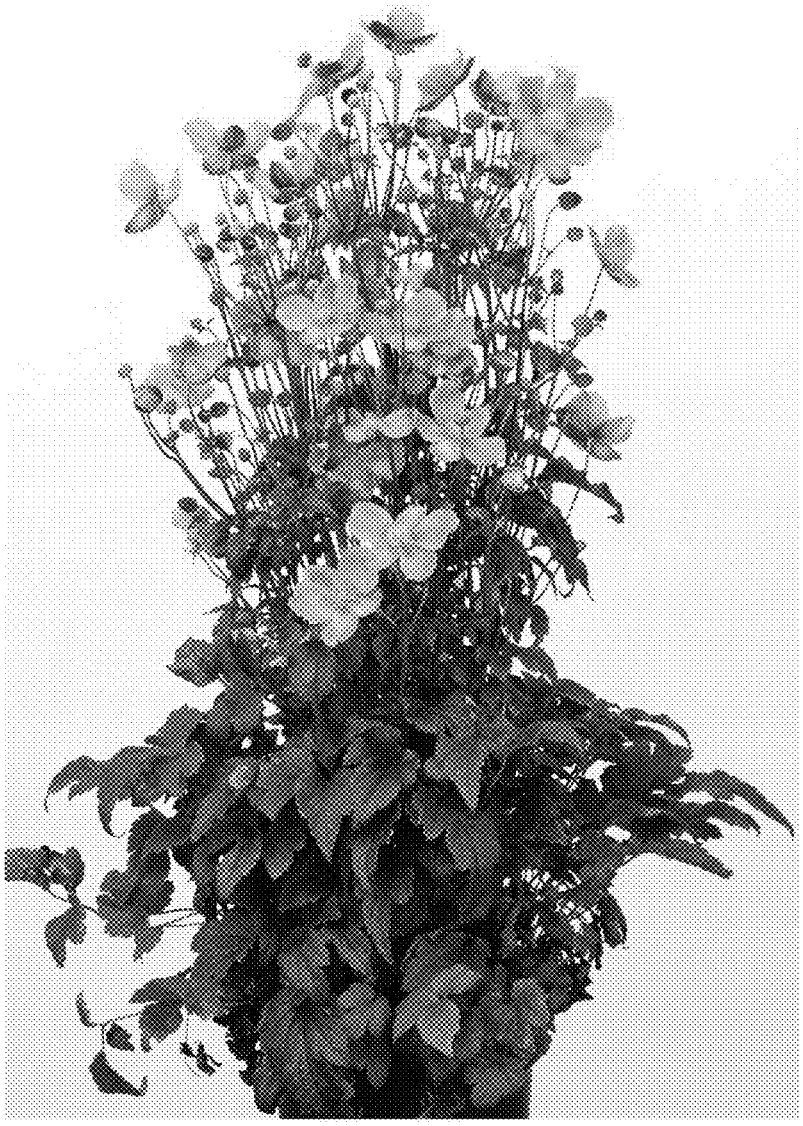

Botanical designation: *Anemone hupehensis*.
Cultivar denomination: 'IFANDWNB'.

BACKGROUND OF THE INVENTION

The present invention relates to a new and distinct cultivar of *Anemone*, botanically known as *Anemone hupehensis* and hereinafter referred to by the name 'IFANDWNB'.

The new *Anemone* plant is a product of a planned breeding program conducted by the Inventor in Heerhugowaard, The Netherlands. The objective of the breeding program is to create new vigorous and fast-growing *Anemone* plants with numerous attractive flowers.

The new *Anemone* plant originated from an open-pollination in July, 2013 in a controlled greenhouse environment in Heerhugowaard, The Netherlands of *Anemone hupehensis* 'IFANFJ', disclosed in U.S. Plant Pat. No. 31,777, as the female, or seed, parent with an unknown proprietary selection of *Anemone hupehensis* as the male, or pollen, parent. The new *Anemone* plant was discovered and selected by the Inventor as a single flowering plant within the progeny of the stated open-pollination controlled greenhouse environment in Heerhugowaard, The Netherlands in August, 2024.

Asexual reproduction of the new *Anemone* by in vitro meristem culture in a controlled environment in Heerhugowaard, The Netherlands since October, 2024 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'IFANDWNB'. These characteristics in combination distinguish 'IFANDWNB' as a new and distinct *Anemone* plant:

1. Compact, upright and uniform plant habit.
2. Moderately vigorous to vigorous growth habit.
3. Early and freely flowering habit.
4. Long flowering period.
5. Single-type flowers that are purplish red in color.
6. Good garden performance.

Plants of the new *Anemone* can be compared to plants of the female parent, 'IFANFJ'. Plants of the new *Anemone* differ primarily from plants of 'IFANFJ' in the following characteristics:

1. Plants of the new *Anemone* are more compact than plants of 'IFANFJ'.
2. Plants of the new *Anemone* flower earlier than plants of 'IFANFJ'.
3. Flowers of plants of the new *Anemone* are darker in color than flowers of plants of 'IFANFJ'.

Plants of the new *Anemone* can be compared to plants of *Anemone hupehensis* 'IFANFA', disclosed in U.S. Plant Pat. No. 34,891. In side-by-side comparisons, plants of the new *Anemone* and 'IFANFA' differ primarily in the following characteristics:

1. Plants of the new *Anemone* are more compact than plants of 'IFANFA'.
2. Plants of the new *Anemone* flower earlier than plants of 'IFANFA'.
3. Flowers of plants of the new *Anemone* have fewer sepals than flowers of plants of 'IFANFA'.

4. Flowers of plants of the new *Anemone* are darker in color than flowers of plants of 'IFANFA'.

Plants of the new *Anemone* can be compared to plants of *Anemone hupehensis* 'IFANELS', not patented. In side-by-side comparisons, plants of the new *Anemone* and 'IFANELS' differ primarily in the following characteristics:

1. Plants of the new *Anemone* are more compact than plants of 'IFANELS'.
2. Plants of the new *Anemone* flower earlier than plants of 'IFANELS'.
3. Flowers of plants of the new *Anemone* are purplish red in color whereas flowers of plants of 'IFANELS' are white in color.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet (FIG. 1) is a side perspective view of a typical plant of 'IFANDWNB' grown in a container.

Figure 2:
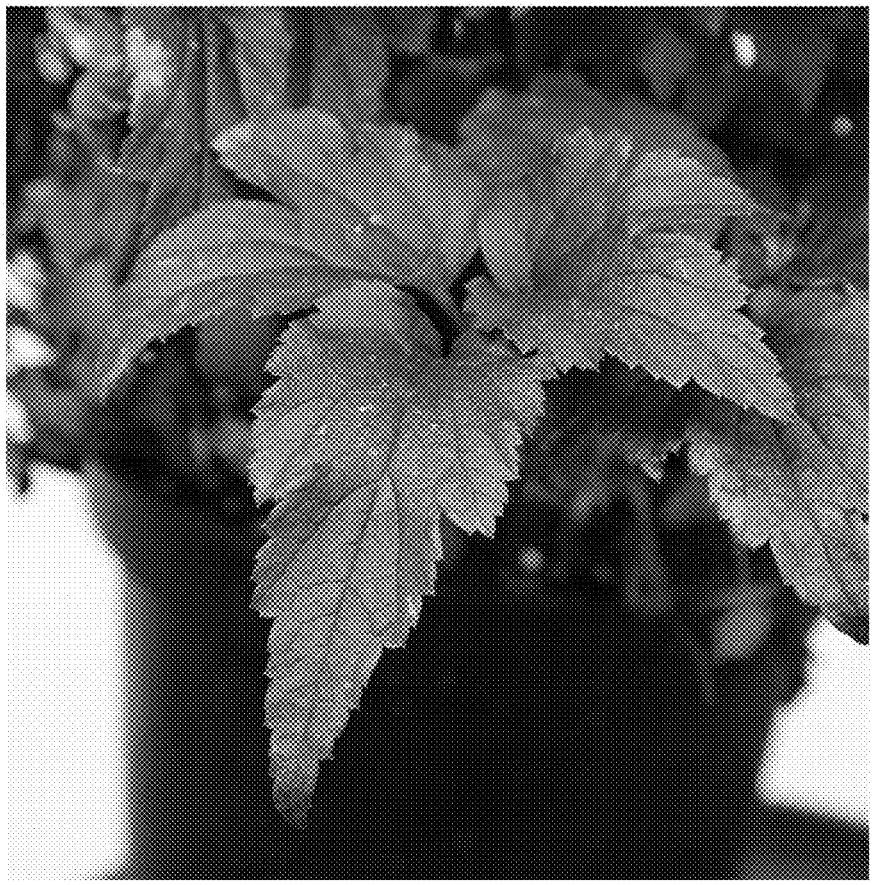

The photograph on the second sheet (FIG. 2) is a close-up view of typical leaves of 'IFANDWNB'.

Figure 3:
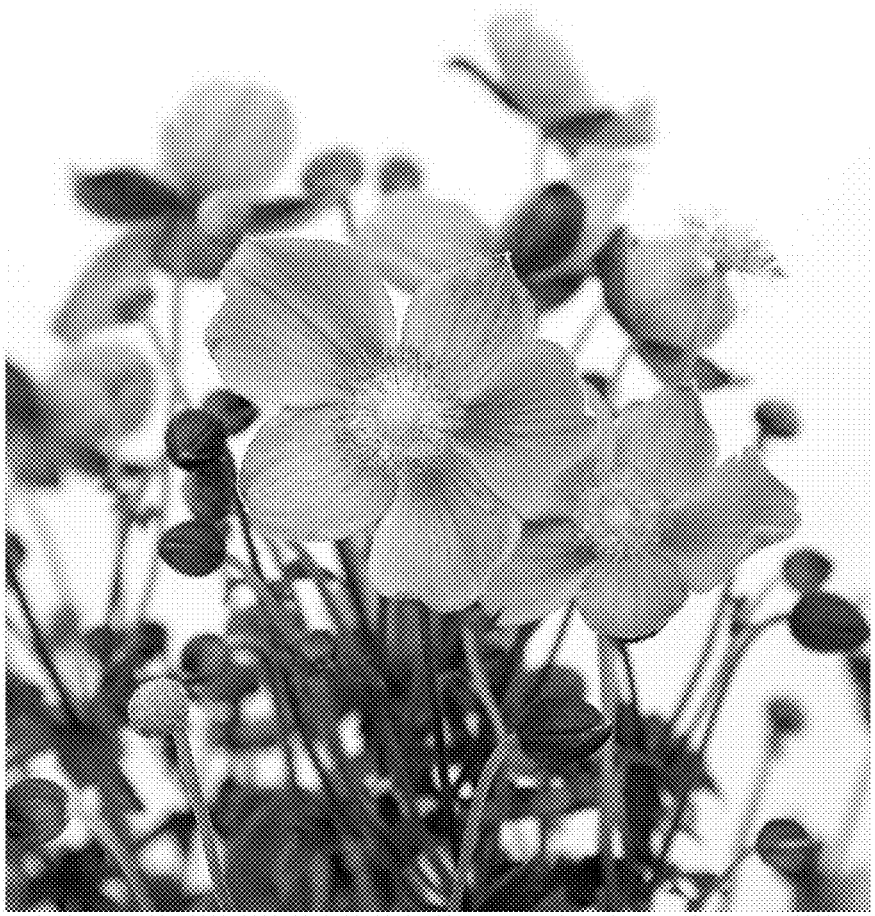

The photograph on the third sheet (FIG. 3) is a close-up view of typical flowers of 'IFANDWNB'.

DETAILED BOTANICAL DESCRIPTION

The aforementioned photographs and following observations, measurements and values describe plants grown during the late summer/early autumn in 15-cm containers in an outdoor nursery in Heerhugowaard, The Netherlands and under cultural practices typical of commercial *Anemone* production. During the production of the plants, day temperatures ranged from 16° C. to 30° C. and night temperatures ranged from 8° C. to 18° C. Plants were eight months old when the photographs and description were taken. In the following description, color references are made to The Royal Horticultural Society Colour Chart, 2015 Edition, except where general terms of ordinary dictionary significance are used.

Botanical classification: *Anemone hupehensis* 'IFANDWNB'.

Parentage:

*Female, or seed, parent.*—*Anemone hupehensis* 'IFANFJ', disclosed in U.S. Plant Pat. No. 31,777.

*Male, or pollen, parent.*—Unknown selection of *Anemone hupehensis*, not patented.

Propagation:

*Type.*—In vitro meristem culture.

*Time to initiate roots, summer.*—About ten days at temperatures about 22° C.

*Time to initiate roots, winter.*—About 15 days at temperatures about 20° C.

*Time to produce a rooted young plant, summer.*—About 42 days at temperatures about 20° C.

*Time to produce a rooted young plant, winter.*—About 50 days at temperatures about 20° C.

*Root description.*—Thin, fibrous; typically close to N199C to N199D in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial; upright and uniform plant habit with basal stems and leaves developing in basal rosettes; numerous basal rosettes developing per plant; plants ovate in overall shape; moderately vigorous to vigorous growth habit; moderate growth rate.

*Plant height, soil level to top of foliar plane.*—About 39.1 cm.

*Plant height, soil level to top of floral plane.*—About 60.4 cm.

*Plant diameter.*—About 51 cm.

Branch description:

*Quantity per plant.*—About 35.

*Length.*—About 28.3 cm.

*Diameter.*—About 4 mm.

*Internode length.*—About 18 cm.

*Strength.*—Strong.

*Aspect.*—Upright to about 5° from vertical.

*Texture and luster.*—Densely pubescent; moderately glossy.

*Color, developing.*—Close to 144A to 144B.

*Color, developed.*—Close to between 143A and 144A.

Leaf description:

*Arrangement, basal leaves.*—Alternate; compound.

*Arrangement, stem or cauline leaves.*—Opposite; simple or compound.

*Length, basal leaves.*—About 13.6 cm.

*Width, basal leaves.*—About 11.8 cm.

*Length, cauline leaves.*—About 8.9 cm.

*Width, cauline leaves.*—About 6.4 cm.

*Length, basal and cauline leaflets.*—About 7.7 cm.

*Width, basal and cauline leaflets.*—About 6.4 cm.

*Shape, basal leaves.*—Trifoliate; broadly ovate in overall outline; slightly carinate.

*Shape, cauline leaves.*—Palmately lobed to palmately cleft; broadly ovate in overall outline; slightly carinate.

*Shape, basal and cauline leaflets.*—Ovate to elliptic.

*Apex, basal and cauline leaves and leaflets.*—Acute.

*Base, basal leaves and leaflets.*—Truncate to hastate.

*Base, cauline leaves and leaflets.*—Obtuse to hastate.

*Margin, basal and cauline leaves and leaflets.*—Biserrate.

*Texture and luster, basal leaves and leaflets, upper surface.*—Sparsely pubescent; slightly glossy.

*Texture and luster, basal leaves and leaflets, lower surface.*—Moderately pubescent; matte.

*Texture and luster, cauline leaves and leaflets, upper surface.*—Smooth, glabrous; slightly glossy.

*Texture and luster, cauline leaves and leaflets, lower surface.*—Sparsely pubescent; matte.

*Venation pattern, basal and cauline leaflets.*—Lacinate.

*Color, basal and cauline leaves and leaflets.*—Developing leaves and leaflets, upper surface: Close to 143A. Developing leaves and leaflets, lower surface: Close to 146B. Fully expanded leaves and leaflets, upper surface: Close to between NN137A and 147A; venation, close to 144A. Fully expanded leaves and leaflets, lower surface: Close to 147B; venation, close to 146C to 146D.

*Leaf petioles*.—Length, basal leaves: About 16.8 cm. Diameter, basal leaves: About 2 mm. Length, cauline leaves: About 2.6 cm. Diameter, cauline leaves: About 1.5 mm. Strength, basal and cauline leaves: Strong. Texture and luster, basal and cauline leaves, upper and lower surfaces: Moderately pubescent; slightly glossy. Color, basal and cauline leaves, upper surface: Close to 144A slightly tinged with close to 187B. Color, basal and cauline leaves, lower surface: Close to 144A slightly to moderately tinged with close to 187B.

Flower description:

*Flower arrangement and flowering habit*.—Single-type rotate flowers arranged in terminal compound cymes; freely flowering habit with ten flowers per inflorescence and about 350 flowers developing per plant during the flowering season; flowers face upright to slanting outwardly.

*Fragrance*.—None detected.

*Natural flowering season*.—Plants of the new *Anemone* flower during the late summer into the autumn (August to October) in The Netherlands.

*Flower longevity*.—Depending on temperature, individual flowers last about seven to ten days on the plant; flowers not persistent.

*Inflorescence height*.—About 23 cm.

*Inflorescence diameter*.—About 13.1 cm.

*Flower diameter*.—About 5.6 cm.

*Flower length* (*depth*).—About 1.4 cm.

*Flower buds*.—Length: About 1.3 cm. Diameter: About 1 cm. Shape: Ovate. Texture and luster: Moderately pubescent; matte. Color: Close to 187B; proximally, close to 150C.

*Petals*.—Absent.

*Sepals*.—Quantity and arrangement: About five, occasionally six, arranged in a single whorl. Length: About 3.2 cm. Width: About 2.4 cm. Shape: Elliptic to broadly obovate; moderately concave. Apex: Obtuse. Base: Cuneate. Margin: Entire; moderately undulate. Texture and luster, upper surface: Smooth, glabrous; moderately velvety; not rugose; matte. Texture and luster, lower surface: Densely pubescent; not rugose; slightly glossy. Color: When opening, upper surface: Close to 64B and 70B. When opening, lower surface: Close to 75A and 71A. Fully opened, upper surface: Close to 71C to 71D; towards the margins and apex, close to 71D; venation, close to 71B to 71C; color does not change with subsequent development. Fully opened, lower surface: Close to N77B; towards the margins and apex, close to 75A; venation, close to N77B; color does not change with subsequent development.

*Sepaloids*.—To date, sepaloid development has not been observed on plants of the new *Anemone*.

*Peduncles*.—Length: About 12.7 cm. Diameter: About 2 mm. Aspect: About 20° from lateral branch axis. Strength: Strong. Texture and luster: Moderately pubescent; moderately glossy. Color: Close to 143A; surfaces exposed to sunlight are variably tinged with close to 187A.

*Pedicels*.—Length: About 9.2 cm. Diameter: About 1.5 mm. Aspect: Upright to about 30° from the peduncle axis. Strength: Moderately strong. Texture and luster: Densely pubescent; slightly glossy. Color: Close to 146B; distally, close to 197B to 197C.

*Reproductive organs*.—Androecium: Stamen number per flower: About 250. Filament length: About 6 mm. Filament color: Close to 155C. Anther shape: Oblong. Anther size: About 0.5 mm by 1.5 mm. Anther color: Close to 14A. Amount of pollen: Moderate. Pollen color: Close to 11D. Gynoecium: Pistil number per flower: About 400. Pistil length: About 0.75 mm. Stigma shape: Club-shaped. Stigma size: About 0.2 mm by 0.2 mm. Stigma color: Close to 150C. Style length: About 0.55 mm. Style color: Close to 144C. Ovary color: Close to 145D.

*Seeds and fruits*.—To date, seed and fruit development have not been observed on plants of the new *Anemone*.

Garden performance: Plants of the new *Anemone* have been observed to have good garden performance and to tolerate temperatures ranging from about −30° C. to about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'IFANDWNB' as herein illustrated and described.

* * * * *